United States Patent [19]
Kurahashi et al.

[11] Patent Number: 4,560,652
[45] Date of Patent: Dec. 24, 1985

[54] PROCESS FOR PRODUCING L-TRYPTOPHAN BY FERMENTATION

[75] Inventors: Osamu Kurahashi, Kawasaki; Masahiro Kamada, Yokohama; Hitoshi Enei, Zushi, all of Japan

[73] Assignee: Ajinomoto Co., Inc., Tokyo, Japan

[21] Appl. No.: 444,172

[22] Filed: Nov. 24, 1982

[30] Foreign Application Priority Data

Nov. 27, 1981 [JP] Japan .................................. 56-190071

[51] Int. Cl.$^4$ ........................ C12P 13/22; C12N 15/00; C12R 1/125
[52] U.S. Cl. ................................. 435/108; 435/172.1; 435/839
[58] Field of Search ............... 435/108, 172, 253, 243, 435/244, 245, 832, 839

[56] References Cited

U.S. PATENT DOCUMENTS

| | | | |
|---|---|---|---|
| 3,700,558 | 10/1972 | Thiemann et al. | 435/108 |
| 3,700,559 | 10/1972 | Shiio et al. | 435/108 |
| 3,801,457 | 4/1974 | Arima et al. | 435/108 |
| 3,849,251 | 11/1974 | Nakayama et al. | 435/108 |
| 4,363,875 | 12/1982 | Akashiba et al. | 435/108 |

FOREIGN PATENT DOCUMENTS

| | | | |
|---|---|---|---|
| 6092796 | 7/1981 | Japan | 435/108 |
| 0208994 | 12/1982 | Japan | 435/108 |
| 0080378 | 6/1983 | Japan | 435/108 |
| 0081107 | 6/1983 | Japan | 435/108 |

OTHER PUBLICATIONS

*Chemical Abstracts*, vol. 92, No. 17, p. 279, Abstract No. 143110(w), Bazzicalupo, M. et al., "Characterization of 5-Fluoroindole and 5-Fluorotryptophan Resistant Mutants in *Bacillus subtilis*".
*The Merck Index*, 9th Edition, Windholtz, M. et al. ed., Merck and Co., Inc., Rahway, N.J., p. 240 (1976).
*Metabolic Inhibitors*, vol. I, Hochster, R. M. et al., ed., Academic Press, New York, pp. 53–57, 215–218 (1963).

*Primary Examiner*—Thomas G. Wiseman
*Assistant Examiner*—Dinah Lewitan
*Attorney, Agent, or Firm*—Oblon, Fisher, Spivak, McClelland & Maier

[57] ABSTRACT

A process for economically producing L-tryptophan which involves culturing aerobically in a culture medium a mutant of the genus Bacillus which is resistant to azaserine and a tryptophan analogue and recovering the L-tryptophan produced which accumulates in the culture medium.

8 Claims, No Drawings

PROCESS FOR PRODUCING L-TRYPTOPHAN BY FERMENTATION

BACKGROUND OF THE INVENTION

1. Field of the Invention

This invention relates to a process for producing L-tryptophan by fermentation.

2. Description of the Prior Art

It was known prior to the present invention that L-tryptophan, which is one of the essential amino acids and is an essential component in human and animal nutrition, can be synthesized by a variety of methods, some of which involve starting with β-indolylaldehyde and hippuric acid, e.g., Berichte, 39, 2515 (1906), and some of which involve starting with o-ketoglutaric acid and phenyl hydrazone, e.g., U.S. Pat. No. 3,019,232. In addition to these chemical synthetic processes, it was known that L-tryptophan can be produced from precursors such as an anthranilic acid, indole, or 3-indole pyruvate by the action of microorganisms.

It was also known that L-tryptophan can be produced by a fermentation process in which L-tryptophan-producing mutants of the genus Brevibacterium are used; various L-tryptophan-producing mutants produced by the artifical mutation of wild strains of microorganisms of the genera Brevibacterium, Corynebacterium, or Bacillus are known.

Examples of such artifical mutants are mutants resistant to tryptophan analogues, such as 5-methyl tryptophan (as disclosed in Japanese Published Examined Patent Application Nos. 18828/1973 and 39517/1978); mutants resistant to tryptophan analogues and phenylalanine analogues; and mutants resistant to these analogues and requiring an L-amino acid such as L-tyrosine, L-phenylalanine, L-methionine, or L-histidine for their growth (as disclosed in Japanese Published Unexamined Patent Application Nos. 42091/1975 and 129791/1975, Japanese Published Examined Patent Application No. 19037/1976, and *Agr. Biol. Chem.*, 39, 343 (1975)).

Recently, there has been a great demand for L-tryptophan as a feed stuff, but this demand cannot be met because L-tryptophan cannot be produced at a reasonable price by any known fermentation process or chemical synthetic process even though various processes for producing L-tryptophan are known.

SUMMARY OF THE INVENTION

Accordingly, it is an object of this invention to provide a process for producing L-tryptophan in high yield by fermentation.

It is a further object of this invention to provide a process for producing L-tryptophan by fermentation in a commercially feasible process.

These and other objects of the invention as will hereinafter become more readily apparent have been accomplished by providing a process for producing L-tryptophan by fermentation, which comprises culturing aerobically in a culture medium a mutant of the genus Bacillus which is resistant to azaserine and a tryptophan analogue and is capable of producing L-tryptophan and recovering the L-tryptophan which accumulates in the culture medium.

DESCRIPTION OF THE PREFERRED EMBODIMENTS

The process of the present invention makes it possible to produce L-tryptophan in improved yield by a fermentation process.

More particularly, the production of L-tryptophan can be increased when resistance to azaserine is imparted to a known tryptophan-analogue-resistant and L-tryptophan-producing mutant of the genus Bacillus.

The microorganisms employed in the process of the present invention are mutants which belong to the genus Bacillus and are resistant to azaserine and a tryptophan anlogue and are capable of producing L-tryptophan in a high yield. Prior to the present invention it was not known that tryptophan production could be increased by making a tryptophan-analogue-resistant microorganism also resistant to azaserine.

Azaserine (also known as serine diazoacetate or O-diazoacetyl-L-serine) is one of the antibiotics produced by microorganisms of the genus Streptomyces having antineoplastic activity and is known as one of the glutamine antagonists.

Tryptophan analogues, in the manner in which the term is used in connection with the present invention, are those chemicals which normally inhibit the growth of microorganisms of the genus Bacillus in the absence of L-tryptophan, the inhibition being suppressed when L-tryptophan coexists in the medium. The tryptophan analogues include lower alkyltryptophans, such as 5-methyltryptophan and 6-methyltryptophan; halotryptophans, such as 5-fluorotryptophan and 6-fluorotryptophan; tryptophan hydroxamate; and 7-azatryptophan.

According to a preferred embodiment of the present invention, known characteristics useful for the production of L-tryptophan, such as a requirement for L-phenylalanine, L-leucine, or L-methionine in the growth medium, and resistance to a phenylalanine analogue, are imparted to the mutants used in the process of the present invention, even though the original mutant having such characteristics does not produce L-tryptophan prior to being made resistant to azaserine and a tryptophan analogue.

Representative mutants of the present invention include:

Bacillus subtilis AJ 11709; FERM-P 6225, FERM-BP 200 (5-F-Trp$^r$, AS$^r$);

Bacillus subtilis AJ 11710; FERM-P 6226, FERM-BP 201 (5-F-Trp$^R$, Leu$^-$, AS$^r$); and Bacillus subtilis AJ 11716; FERM-P 6227, FERM-BP 202 (5-F-Trp$^r$, IM$^r$, AS$^r$)

wherein the abbreviations in parentheses have the following meanings:

5-F-Trp$^r$: resistance to 5-fluorotryptophan;

AS$^r$,IM$^r$: resistance to azaserine and to indolmycin;

Leu$^-$: requirement for L-Leucine for their growth.

The mutants identified above by FERM-P numbers were originally deposited on Nov. 18, 1981 at the Fermentation Research Institute, Agency of Industrial Sciences and Technology, Ministry of International Trade and Industry (FRI), 1-3, Migashi 1-Chome, Yatebemachi, Tsukuba-gun, Ibnaragi-ken 305, Japan, and were accorded the FERM-P number indicated above. The mutant deposits were then converted into deposits under the Budapest Treaty on Oct. 25, 1982, and were accorded the corresponding FERM-BP numbers.

The mutants employed in the process of the present invention can be induced from parent microorganism strains by any conventional mutation method. Typically, the first step of induction is to mutate the parent strain with a suitable chemical mutagen, such as N-methyl-N'-nitro-N-nitrosoguanidine or nitrous acid, or with irradiation by ultraviolet light. The second step of the process is to select resistant mutants by picking up colonies of the microorganisms grown on plates of a nutrient agar medium containing an amount of azaserine which inhibits the growth of the parent strains. Thereafter, the mutants are evaluated for L-tryptophan production by a standard method.

Suitable parent strains from which the present mutants can be induced include mutants of the genus Bacillus which are resistant to a tryptophan analogue and which are capable of producing L-tryptophan and wild strains of the genus Bacillus.

The preferred mutants resistant to tryptophan analogue are, for example: *Bacillus subtilis* FT-145; FERM-P 1783 (5-F-Tr$^r$); *Bacillus subtilis* FFL-5; FERM-P 1786 (5-F-Trp$^r$, Leu$^-$); and *Bacillus subtilis* AJ 11483; FERM-P 5286 (5-F-Trp$^r$, Im$^r$). FERM-P 1783 and 1786 (as disclosed in Japanese Published Examined Patent Application No. 39517/1978) were deposited on Dec. 19, 1972, and FERM-P 5286 (as disclosed in Japanese Published Unexamined Patent Application No. 92796/1981) was deposited on Dec. 5, 1979.

When a wild strain is used as the parent strain, resistance to a tryptophan analogue is imparted to the wild strain either prior to or after imparting resistance to azaserine to the wild strain.

The degree of resistance to azaserine of the mutants as stated above are shown in the following Experiment.

Experiment

Agar plates (8.5 cm in diameter) containing the minimum medium having the composition given in Table 1 and further containing 100 microgram/ml azaserine were prepared.

TABLE 1

| Composition of Minimum Medium (pH 7.0) | |
|---|---|
| Component | Amount per 1.0 liter |
| Glucose | 5.0 g |
| Ammonium sulfate | 1.0 g |
| KH$_2$PO$_4$ | 8.65 g |
| MgSO$_4$.7 H$_2$O | 0.2 g |
| FeSO$_4$.7 H$_2$O | 10 mg |
| MnSO$_4$.4 H$_2$O | 10 mg |
| Sodium citrate | 0.5 g |
| L-Leucine* | 100 mg |
| Agar | 20 g |

*L-Leucine was added only when AJ 11710 was used

Each strain grown on an agar slant of the mimimum medium was inoculated on the plate; the inoculum size was adjusted to 10$^6$ cells per plate. Then the plate was incubated at 30° C. for 2 days and the number of colonies of the microorganisms grown on the plate were counted. The results obtained are shown in Table 2.

TABLE 2

| | Degree of resistance |
|---|---|
| Strain | Number of colonies per plate |
| FT-145 | 0 |
| AJ 11709 | 500 |
| AJ 11710 | more than 1000 |
| AJ 11716 | more than 1000 |

The mutants of the present invention are cultured aerobically in a culture medium containing a carbon source, a nitrogen source, inorganic ions and, when required, minor nutrients.

Suitable carbon sources include saccharides, such as glucose, fructose, and sucrose; molasses or hydrolyzed starch containing these saccharides; organic acids, such as acetic acid and citric acid; and alcohols. Suitable nitrogen sources include, for example, ammonium sulphate, ammonium nitrate, gaseous ammonia, and urea. As the inorganic ions, K$^+$, Na$^+$, Ca$^{++}$, Fe$^{++}$, Mn$^{++}$, Mg$^{++}$, Zn$^{++}$, SO$_4^{--}$, Cl$^-$, and PO$_4^{---}$ ions are suitably added to the culture medium where required.

Suitable minor nutrients include amino acids, vitamins, yeast extract, peptone, and hydrolyzed soy protein and may be added if desired. When mutants require nutrient elements such as an L-amino acid, the nutrient is added to the culture medium.

Cultivation is carried out preferably under aerobic conditions. Cultivation for from 1 to 4 days at a temperature ranging from 20°to 40° C. is convenient. It is preferable to adjust the pH of the culture medium to the range from 5.0 to 9.0 with an organic or inorganic acid or alkali. For this purpose, urea, CaCO$_3$, and gaseous ammonia are preferably used. Hydrochloric acid is a preferred acid.

The L-tryptophan accumulated in the culture medium may be recovered by an entirely conventional recovering technique, such as those which use an anion-exchange resin.

Having generally described this invention, a more complete understanding can be obtained by reference to the following specific example which is provided herein for purpose of illustration only and is not intended to be limiting unless otherwise specified.

EXAMPLE

Twenty ml portions of the culture medium having the composition given in Table 3 were placed in 500 ml flasks which were then heated at 110° C. for 10 minutes. Thereafter, each flask was supplemented with 1.0 g CaCO$_3$ separately sterilized.

TABLE 3

| Composition of Culture Medium (pH 7.0) | |
|---|---|
| Component | Amount per 1.0 liter |
| Glucose | 80 g |
| Ammonium chloride | 10 g |
| KH$_2$PO$_4$ | 1.0 g |
| KCl | 2.0 g |
| MnSO$_4$.7 H$_2$O | 10 mg |
| FeSO$_4$.4 H$_2$O | 10 mg |
| MgSO$_4$.7 H$_2$O | 0.4 g |
| Hydrolyzed casein | 4 g |

Each strain shown in Table 4, which was previously cultured on an agar slant of the same culture medium, was inoculated into a batch of the culture medium and cultured with shaking at 30° C. for 96 hours in order to test its production of L-tryptophan. After this cultivation, the amount of L-tryptophan which accumulated in the culture broth was determined according to a standard bio-assay method using *Leuconostoc mesenteroides* ATCC 8042. The results obtained are shown in Table 4.

TABLE 4

| Amount of L-tryptophan accumulated | |
|---|---|
| Strain No. | L-Tryptophan (mg/ml) |
| FT-145 (5-F-Trp$^r$) | 1.90 |

TABLE 4-continued

| Amount of L-tryptophan accumulated | |
|---|---|
| Strain No. | L-Tryptophan (mg/ml) |
| AJ 11709 (5-F-Trp$^r$, AS$^r$) | 3.5 |
| AJ 11710 (5-F-Trp$^r$, Leu$^-$, AS$^r$) | 7.0 |
| AJ 11716 (5-F-Trp$^r$, IM$^r$, AS$^r$) | 7.1 |

Culture broth of AJ 11716 prepared in the same manner as described above was collected and centrifuged to remove microbial cells and solid $CaCO_3$. One liter of supernatant solution thus obtained was passed through a column of Daiaion SK 104 (a typical anion-exchange resin) in the acid form. By this procedure L-tryptophan was adsorbed on the resin and later eluted with 0.5 N $NH_4OH$. The eluent was evaporated and cooled to a temperature low enough to crystallize L-tryptophan. Then crude crystalline L-tryptophan was dissolved in an aliquot of 50% ethanol solution and active carbon was added to the solution. After decolorization was carried out, 4.5 g of crystalline L-tryptophan were obtained from the decolorized solution.

The invention now being fully described, it will be apparent to one of ordinary skill in the art that many changes and modifications can be made thereto without departing the spirit or scope of the invention as set forth herein.

What is claimed as new and desired to be secured by Letter Patent of the United States:

1. A process for producing L-tryptophan by fermentation, which comprises:
   culturing aerobically in a culture medium containing a source of carbon, nitrogen and inorganic ions and minor nutrients an L-tryptophan-producing mutant of *Bacillus subtilis* which is resistant to azaserine and a tryptophan antagonist under conditions and for a time sufficient to produce L-tryptophan; and recovering the L-tryptophan which accumulates in the culture medium.

2. A process according to claim 1, wherein the mutant belongs to the species *Bacillus subtilis*.

3. A process according to claim 1, wherein the tryptophan analogue is 5-methyltryptophan or 5-fluorotryptophan.

4. A process according to claim 2, wherein the tryptophan analogue is 5-methyltryptophan or 5-fluorotryptophan.

5. A process according to claim 1, wherein said culture medium, having a pH of 7, comprises glucose, ammonium chloride, $KH_2PO_4$, KCl, $MnSO_4$, $FeSO_4$, $MgSO_4$, $CaCO_3$, and hydrolyzed casein.

6. A process according to claim 1, wherein the mutant is *Bacillus subtilis* AJ 11709, *Bacillus subtilis* AJ 11710, or *Bacillus subtilis* AJ 11716.

7. A process according to claim 3, wherein the mutant is *Bacillus subtilis* AJ 11709, *Bacillus subtilis* AJ 11710, or *Bacillus subtilis* AJ 11716.

8. A process according to claim 5, wherein the mutant is *Bacillus subtilis* AJ 11709, *Bacillus subtilis* AJ 11710, or *Bacillus subtilis* AJ 11716.

* * * * *